(12) United States Patent
Giaever et al.

(10) Patent No.: US 7,332,313 B2
(45) Date of Patent: Feb. 19, 2008

(54) ELECTRICAL WOUNDING ASSAY FOR CELLS IN VITRO

(75) Inventors: Ivar Giaever, Schenectady, NY (US); Charles R. Keese, Schoharie, NY (US)

(73) Assignee: Applied BioPhysics, Inc., Troy, NY (US)

( * ) Notice: Subject to any disclaimer, the term of this patent is extended or adjusted under 35 U.S.C. 154(b) by 555 days.

(21) Appl. No.: 10/163,322

(22) Filed: Jun. 5, 2002

(65) Prior Publication Data
US 2002/0182591 A1 Dec. 5, 2002

Related U.S. Application Data

(60) Provisional application No. 60/295,990, filed on Jun. 5, 2001.

(51) Int. Cl.
*A46B 3/08* (2006.01)
(52) U.S. Cl. ............... 435/173.4; 435/173.5; 435/173.6; 204/164; 204/555; 204/403.01; 204/403.13
(58) Field of Classification Search ............ 435/285.2, 435/286.5, 288.4
See application file for complete search history.

(56) References Cited

U.S. PATENT DOCUMENTS 5,187,096 A   2/1993   Giaever et al.

FOREIGN PATENT DOCUMENTS

JP         363202369 A   *   8/1988

OTHER PUBLICATIONS

Giaever, I and Keese, CR, "A morphological biosensor for mammalian cells," Nature, vol. 366, pp. 591-592, Dec. 9, 1993.

Giaever, I and Keese, CR, "Monitoring fibroblast behavior in tissue culture with an applied electric field," Proc. Natl. Acad. Sci. USA, vol. 81, pp. 3761-3764, Jun. 1984.
Keese, CR and Giaever, I, "A biosensor that monitors cell morphology with electrical fields," IEEE Engineering in Medicine and Biology, pp. 402-408, Jun./Jul. 1994.
Reddy, L et al., "Assessment of rapid morphological changes associated with elevated cAMP levels in human orbital fibroblasts," Experimental Cell Research 245, pp. 360-367, 1998.
Keese, CR et al., "Cell-substratum interactions as a predictor of cytotoxicity," In Vitro & Molecular Toxicology, vol. 11, No. 2, pp. 183-192, 1998.
Giaever, I and Keese, CR, "Micromotion of mammalian cells measured electrically,", Proc. Natl. Acad. Sci. USA, vol. 88, pp. 7896-7900, Sep. 1991.
Mitra, P, Keese, CR and Giaever, I, "Electric measurements can be used to monitor the attachment and spreading of cells in tissue culture," BioTechniques (The Journal of Laboratory Technology for Bio-research), vol. 11, No. 4, pp. 504-510, Oct. 1991.
Tiruppathi, C et al., "Electrical method for detection of endothelial cell shape change in real time: Assessment of endothelial barrier function," Proc. Natl. Acad. Sci. USA, vol. 89, pp. 7919-7923, Sep. 1992.
DePaola, N et al., "Electrical impedance of cultured endothelium under fluid flow," Annals of Biomedical Engineering, vol. 29, pp. 1-9, 2001.
Wegener J, Keese, CR and Giaever, I, "Electric cell-substrate impedance sensing (ECIS) as a noninvasive means to monitor the kinetics of cell spreading to artifical surfaces," Experimental Cell Research 259, pp. 158-166, 2000.

* cited by examiner

*Primary Examiner*—David Redding
(74) *Attorney, Agent, or Firm*—Hoffman, Warnick & D'Alessandro, LLC

(57) ABSTRACT

A method and system for electrically wounding and/or monitoring cell activity in vitro. The invention comprises methods and systems for wounding and/or monitoring cells that place a cell culture on a well that has an exposed electrode. The cell culture can then be wounded and/or monitored using the electrode.

15 Claims, 11 Drawing Sheets

ELECTRICAL WOUNDING ASSAY FOR CELLS IN VITRO

REFERENCE TO PRIOR APPLICATION

The current application claims the benefit of co-pending U.S. provisional application Ser. No. 60/295,990, filed on Jun. 5, 2001 and incorporated herein by reference.

BACKGROUND OF THE INVENTION

1. Technical Field

The present invention relates generally to wound healing assays, and more particularly, to a system and method for electrically wounding and/or monitoring a cell culture.

2. Background Art

Wound healing assays have been carried out in tissue culture for many years to monitor cell behavior, including estimating the migration and proliferative capacities of different cells and of cells under different conditions.

These assays generally involve first growing cells to form a confluent monolayer. The monolayer is then disrupted by destroying or displacing a group of cells. Common methods for disrupting the cell monolayer comprise scratching a line (i.e., manually dragging a pointed device) through the layer with any of several different tools such as a needle, razor blade, plastic pipette tip or by removing a small area of cells, e.g., with a spinning circular pad. Additionally, wounding may be carried out using a very small spinning disk to give a more reproducible area to follow. Once a wound is achieved, the wound is then microscopically observed or photographed over time to assess the rate at which the damaged area is filled in by the neighboring cells. The above-mentioned wounding methods require extensive manipulation of the cultured cells, making the wounding methods expensive and, furthermore, difficult to accurately reproduce and to verify experimental results.

As noted, after the disruption is accomplished, the area is inspected microscopically at different time intervals as the cells move in and fill the damaged area. This "healing" can take from several hours to over a day depending on the cell type, growing conditions, and the extent of the "wounded" region. The results may be presented by a series of photomicrographs; or in more sophisticated measurements, the microscopic views may be subjected to image processing such that data can be expressed in quantitative terms.

An alternative form of measuring cell behavior that replaced the commonly used microscopic observations utilizes electrical sensing. One example is disclosed in U.S. Pat. No. 5,187,096, which is hereby incorporated by reference and referred to herein as the "ECIS™ system." Specifically, the ECIS™ system (Electric Cell-substrate Impedance Sensing) sold by Applied Biophysics, Inc., passively analyzes cell behavior by applying a weak AC current and measuring the voltage changes. The device can be used to monitor various cell behaviors, including the morphology changes and cell motions in animal cells that attach and spread out and crawl on the bottom of tissue culture vessels. In the ECIS™ system, cells are grown upon a small gold film electrode ($5 \times 10^{-4}$ $cm^2$) mounted to the bottom of a small well; a much larger counter electrode completes the circuit using standard tissue culture medium as an electrolyte. A weak (e.g., approximately 1 microamp) AC current (usually in the frequency range from 100 to 40,000 Hz) is applied to the system. This small current results in a voltage drop across the small electrode of only a few millivolts. Voltage drops and currents this small do not affect the health of the cells.

Variations in the measured voltage comprise the measurement. As the animal cells attach and spread upon the small electrode, they force the current to flow under and between the cells resulting in changes in impedance and hence, in the measured voltage across the electrode system. These changes can be followed and provide a non-invasive means to monitor changes in cell behavior. For example, using the measured voltages, one can infer cell morphology and cell movements, which are important research measurements that form the basis of many biomedical and biological assays.

While the ECIS™ system allows for automated and passive monitoring of cell behavior following a disruption, the requirement for manipulating the cell culture to create the wound or disruption remains. In addition to requiring human intervention, the current procedure amplifies the possibility of external factors inadvertently affecting the results. Therefore, there exists a need for a wound healing method that provides data that is more quantitative and reproducible than the current methods. In addition, there exists a need for a wound healing method that requires less manipulations and thus less labor in obtaining the experimental results.

SUMMARY OF THE INVENTION

The present invention overcomes the above mentioned problems by providing a system and method that can electrically wound and/or monitor cell behavior with a single device. In one aspect, the invention comprises a system for wounding and monitoring cells, comprising: (A) a self-contained apparatus for processing cell cultures, wherein the apparatus includes: a cell culture holding device having at least one well with an exposed electrode (serving as a substrate for the cells) for holding and contacting a cell culture; an invasive electronic wounding module for generating an electrical current to wound the cell culture in a region proximate the electrode; and a passive electronic monitoring system for determining cell migration of the cell culture by measuring impedance between the electrode and a proximately located counter electrode; and (B) a computer for controlling the self-contained apparatus, the computer having a processor, an I/O, and a memory, wherein the memory contains a software program, which when executed, includes: a wound controller for manipulating the operation of the invasive electronic wounding module; and a monitor controller for manipulating the operation of the passive electronic monitoring system.

The computer software allows a user to read and modify various parameters that control the operation of the apparatus. The computer communicates to the apparatus the various parameters specified by the user and receives back various measurements.

It is therefore an advantage of the present invention to provide a system for creating well defined wounds in cell cultures. It is therefore a further advantage of the present invention to provide a system for wounding and monitoring cells in a single device.

One aspect of the invention provides a method of wounding and monitoring cells, comprising: placing a cell culture in a holding device having at least one well for holding the cell culture, the at least one well having at least one exposed electrode that contacts the cell culture; wounding the cell culture in an area proximate to the at least one electrode; and monitoring the cell culture using the at least one electrode, wherein the cell culture remains isolated during the wounding and monitoring steps.

Another aspect of the invention provides a system for processing a cell culture, comprising: a holding device for maintaining an uninterrupted environment during a wounding and monitoring process, wherein the holding device has at least one well for holding a cell culture, and wherein the at least one well has at least one exposed electrode that contacts the cell culture; a wounding module for wounding the cell culture while the cell culture is in the holding device in an area proximate the at least one electrode; and a monitoring module for monitoring the cell culture while the cell culture is in the holding device.

Still another aspect of the invention provides a system for wounding a cell culture, comprising: a holding device having at least one well for holding the cell culture, the at least one well having at least one exposed electrode that contacts the cell culture; a wounding module for wounding the cell culture using the at least one electrode; and a computer for controlling the wounding module, including: a processor; an I/O; and a memory including a software program, the software program including a wound controller for controlling the operation of the wounding module.

The exemplary aspects of the present invention are designed to solve the problems herein described and other problems not discussed, which are discoverable by a skilled artisan.

BRIEF DESCRIPTION OF THE DRAWINGS

These and other features of this invention will be more readily understood from the following detailed description of the various aspects of the invention taken in conjunction with the accompanying drawings in which.

It is noted that the drawings of the invention are not to scale. The drawings are intended to depict only typical aspects of the invention, and therefore should not be considered as limiting the scope of the invention. In the drawings, like numbering represents like elements between the drawings.

DETAILED DESCRIPTION OF THE INVENTION

One embodiment of the invention comprises a modification of the ECIS™ system that adds an invasive electronic wounding module to wound (e.g., kill) the cells contacting one or more electrodes. Cells in this embodiment may be monitored in a non-invasive mode both before and after the wounding takes place.

Figure 1:
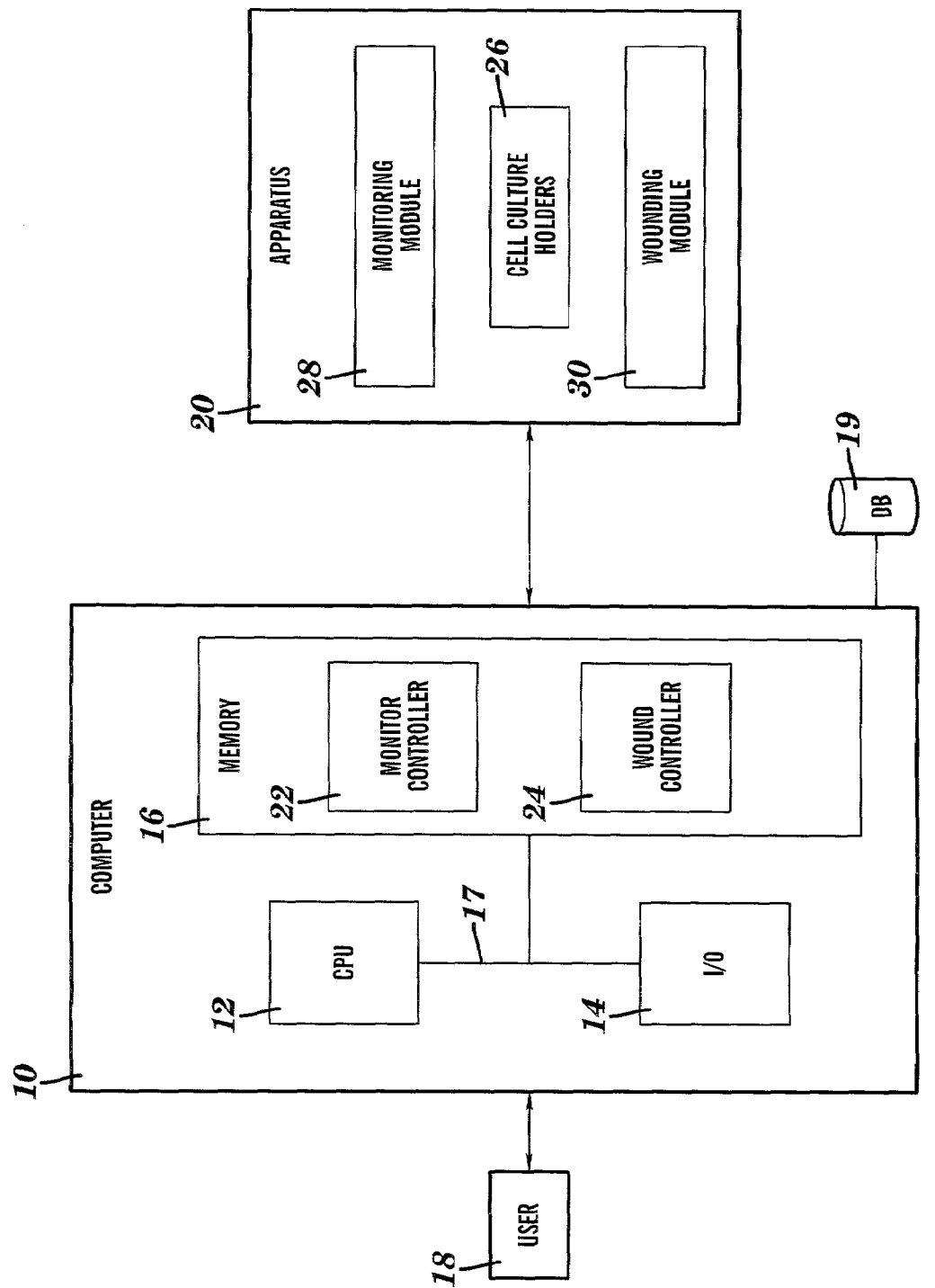
FIG. 1 is a block diagram of a system implementing the invention.

Referring now to the drawings, FIG. 1 illustrates a computer 10, comprising a central processing unit (CPU) 12, input/output (I/O) interface 14, memory 16, and bus 17. A database 19 may also be provided for storage of data relative to processing tasks. Memory 16 and/or database 19 may comprise any known type of data storage and/or transmission media, including magnetic media, optical media, random access memory (RAM), read-only memory (ROM), a data cache, a data object, etc. Moreover, memory 16 and/or database 19 may reside at a single physical location, comprising one or more types of data storage, or be distributed across a plurality of physical systems in various forms. Likewise, CPU 12 may comprise a single processing unit, or be distributed across one or more processing units in one or more locations, e.g., on a client and server. Computer 10 can comprise one or more CPUs 12 utilizing standard operating system software, which is designed to drive the operation of the particular hardware and which is compatible with other system components and I/O controllers. I/O interface 14 may comprise any system for exchanging information with any known type of input/output device including an I/O port (serial, parallel, ethernet, etc.), a universal serial bus (USB) controller, a network system, modem, keyboard, mouse, scanner, voice recognition system, monitor (cathode-ray tube (CRT), liquid-crystal display (LCD), etc.), printer, disc drives, etc. Bus 17 provides a communication link between each of the components in computer 10 and likewise may comprise any known type of transmission link, including electrical, optical, wireless, etc. In addition, although not shown, additional components, such as cache memory, communication systems, system software, etc., may be incorporated into computer 10.

A user 18 can interact with computer 10, which in turn interacts with an apparatus 20. Memory 16 of computer 10 includes a software program that includes a monitor controller 22 and a wound controller 24. Apparatus 20 can be a self-contained unit that allows both wounding and monitoring operations to be performed without removal of the cell cultures from the unit. Apparatus 20 comprises at least one cell culture holder 26, a monitoring module 28, and a wounding module 30. While computer 10 and apparatus 20 are shown separately, it should be recognized that the two may be implemented as a single system.

Figure 2:
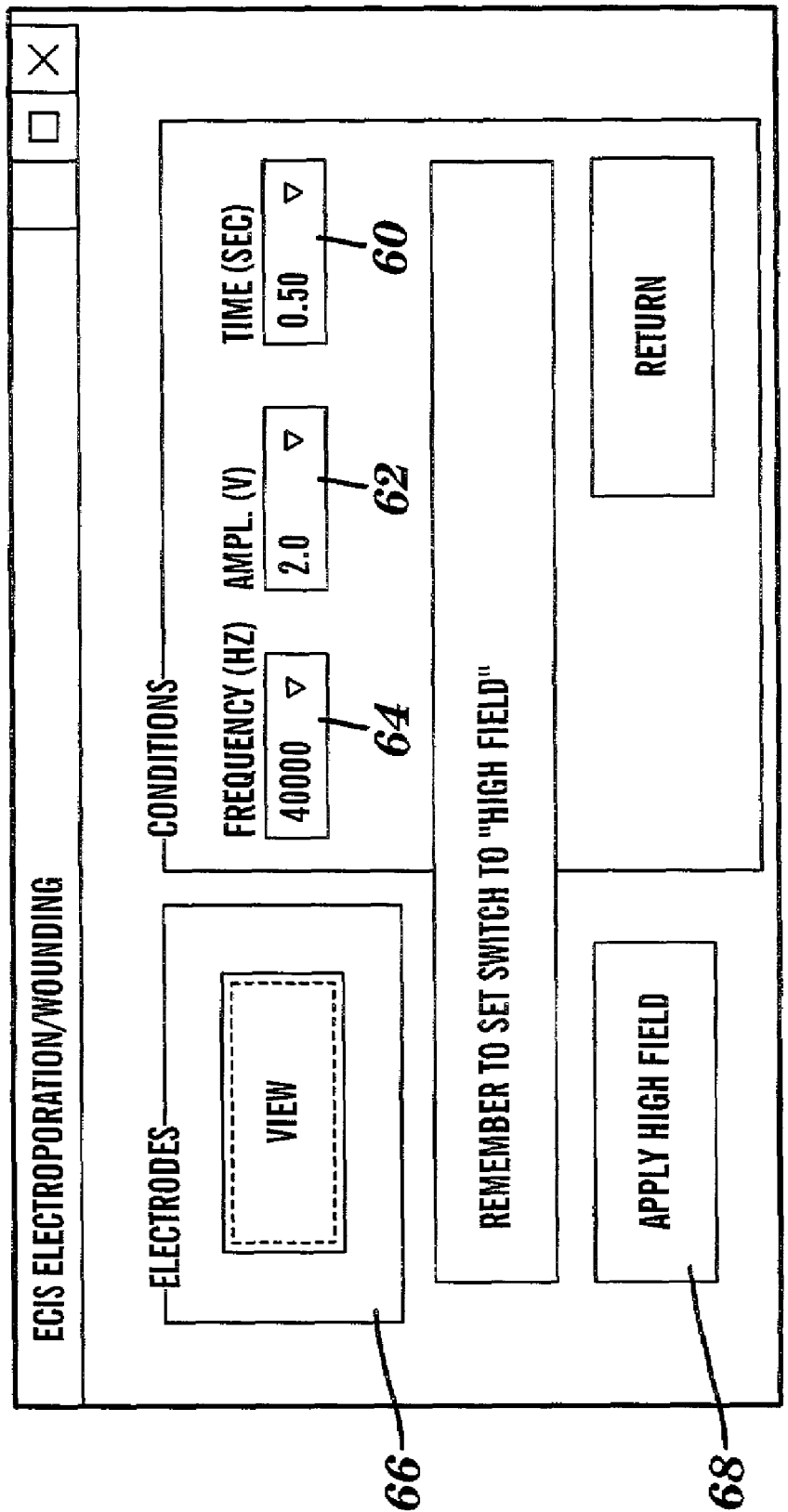
FIG. 2 is an exemplary user interface for setting wounding parameters.

Wounding module 30 receives instructions from wound controller 24 to, for example, selectively apply and maintain a particular current level and/or voltage to electrode(s) in contact with a cell culture in cell culture holder 26. In this case, a high pulse of current can be applied, typically for a few seconds, to wound or electroporate cells in contact with each electrode. FIG. 2 shows an exemplary interface that user 18 can use to interact with wound controller 24 to set up and control the operation of wounding module 30. As shown in FIG. 2, user 18 can specify various attributes of the wounding pulse, for example, a time duration 60, applied voltage (or current) 62, a frequency 64, specific electrodes that will perform the wounding 66, etc. Additionally, user 18 can set a start/stop time for the wounding or immediately perform the wounding by, for example, clicking a button 68. It should be noted that the various attributes of the wounding pulse and/or the start/stop time of the pulse can be the same for all selected electrodes or can be different for each electrode or groups of electrodes. Additionally, while drop-down menus are shown as the interface for numeric values, other interfaces are also possible, for example, an edit box.

Returning to FIG. 1, monitoring module 28 receives instructions from monitor controller 22 and monitors cell cultures in cell culture holder 26. For example, cell culture holder 26 can include one or more electrodes in contact with each cell culture, and a counter electrode. In this case, monitoring module 28 can selectively apply and maintain a particular current level and voltage to each electrode. An electrical characteristic between each electrode and the counter electrode can be measured and communicated to monitor controller 22. Monitor controller 22 can capture, save, and/or display the measurements. For example, monitor controller 22 can store and retrieve data using database 19.

These measurements can be analyzed directly or used to calculate another more desirable characteristic. Any desired electrical characteristic that changes with cell growth can be measured/calculated including, for example, voltage, impedance, capacitance, resistance, etc.

Additionally, more than one electrical characteristic can be measured/calculated for analysis in an experiment. User 18 can interface with monitor controller 22 in a similar fashion as with wound controller 24 and specify, for example, the run time of an experiment, the frequency of measurements, electrical requirements, the types of measurements/calculations, etc. These parameters are then used by monitor controller 22 to control some or all of the operation of monitoring module 28.

Figure 3:
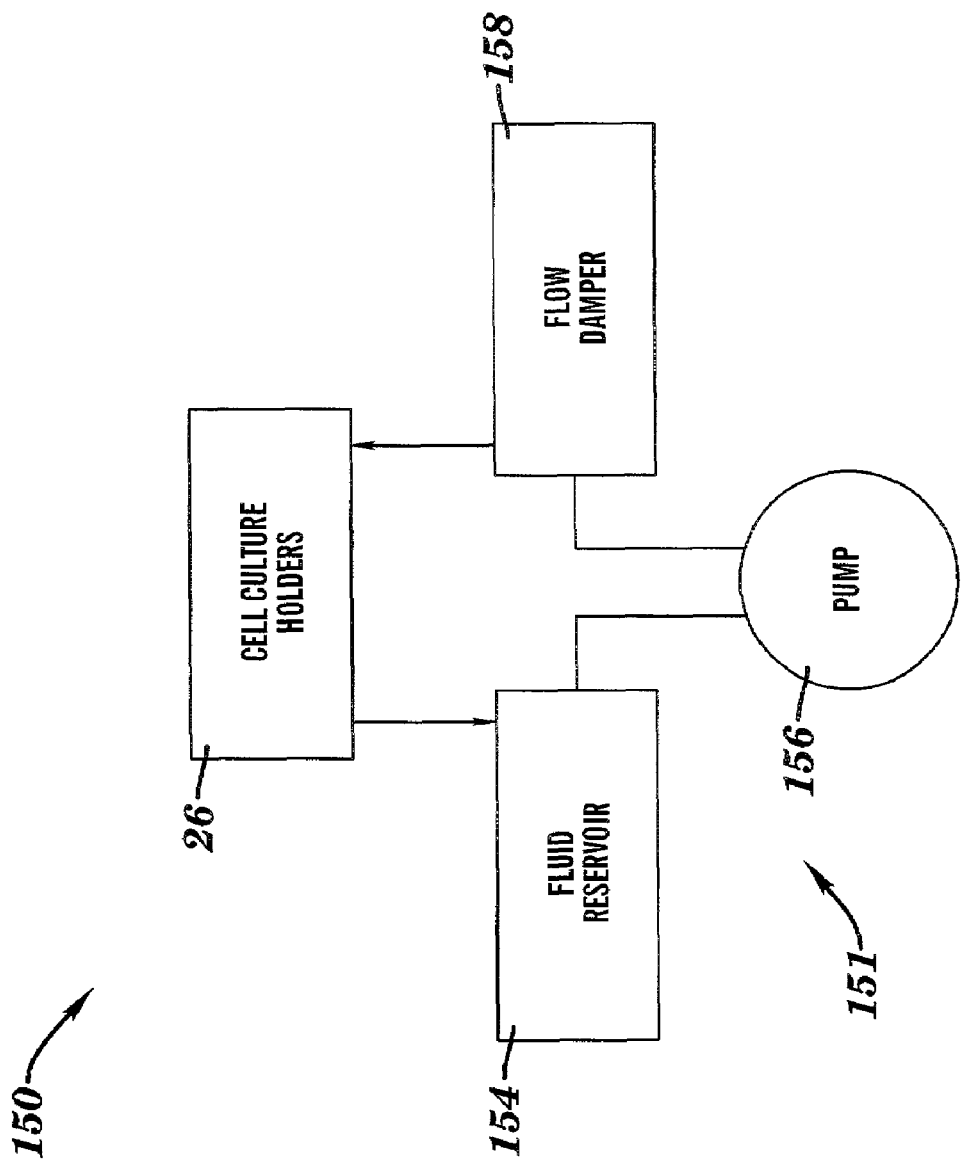
FIG. 3 is a portion of a second system implementing the invention.

A flow module can also be incorporated to further expose a cell culture to the physiological shear stress forces that are exerted by a fluid flowing across the cell culture. FIG. 3 depicts a portion of an exemplary system 150 that includes a flow module 151. Flow module 151 is shown including a fluid reservoir 154, pump 156, and flow damper 158. Pump 156 can force fluid to flow from fluid reservoir 154, through flow damper 158, over cell culture holders 26 and back into fluid reservoir 154. Alternatively, fluid may be stored and retrieved in separate fluid reservoirs so that the same fluid does not flow across cell culture holders 26 during an experiment. The fluid can comprise any liquid or gas, for example, ordinary tissue culture medium, medium containing various biological compounds and/or cells, buffered saline, serum, etc.

Pump 156 and/or flow damper 158 can regulate the flow of fluid such that it flows at varying rates, a steady rate, starts and stops, and/or reverses direction during an experiment. For example, pump 156 can comprise a variable speed peristaltic pump, a reversible pump, a single speed/variable speed pump, gravity feed systems, pressurized flow systems, etc. Pump 156 and/or flow damper 158 can be manually controlled, controlled by software executing in computer 10 (FIG. 1), or a combination thereof.

Figure 4:
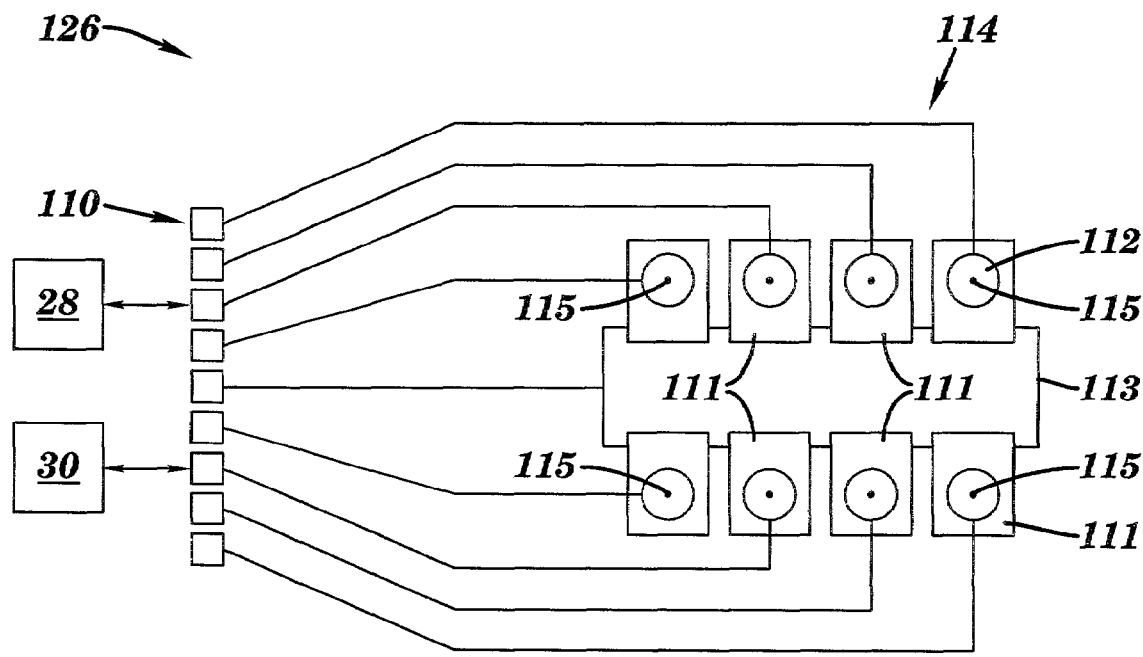
FIG. 4 is a view of a cell culture holder of the invention.

As discussed previously, one aspect of the invention comprises electrically wounding and/or monitoring a cell culture. FIG. 4 illustrates a schematic diagram of a cell culture holder 126 having a plurality of experiment wells 111 configured to electrically wound and/or monitor a cell culture. Individual cell cultures can be selectively placed in one or more of the experiment wells 11. Each experiment well 111 is shown having an electrode support 112 containing an electrode 115. Electrodes 115 are connected to electrical connectors 110 by electrical pathways 114. A counter electrode 113 is situated proximate each electrode 115. Thus, current can pass from electrical connectors 110 along electrical pathways 114 to electrodes 115. Counter electrode 113 provides a return path for the current applied to each electrode 115 after passing through the cell culture and/or an electrically conductive medium.

Figure 5:
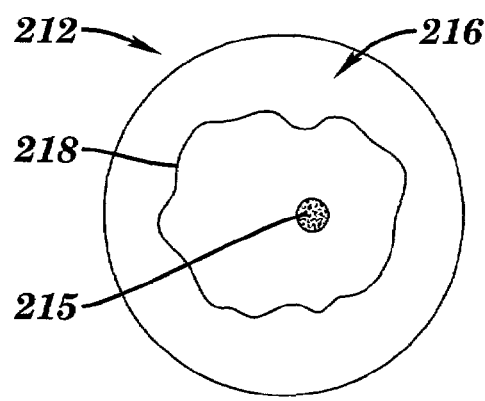
FIGS. 5-6 are exemplary electrodes.
Figure 6:
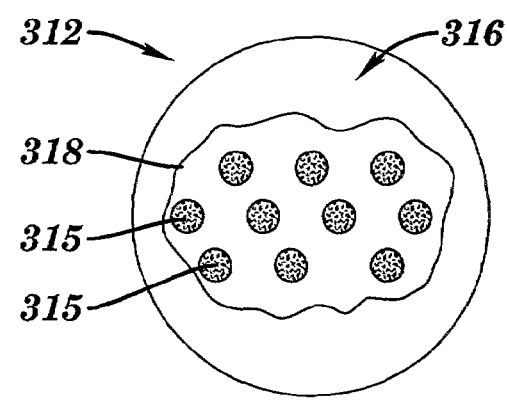

Alternate embodiments of electrode support 112 are shown in FIGS. 5 and 6. FIG. 5 illustrates an electrode support 212 comprising a single electrode 215 surrounded by insulating material 216. FIG. 6 illustrates an electrode support 312 having multiple electrodes 315 surrounded by insulating material 316. It should be recognized that while a certain pattern and number of electrodes 315 are shown, any other patterns and numbers of electrodes 315 are possible and fall within the scope of this invention. Insulating materials 216, 316 can comprise, for example, a very thin layer (e.g., a few micrometers) of insulating material. The insulating material can comprise any insulating material including, for example, various types of photoresist films, other insulating paints, polymers, waxes, etc. Electrodes 215, 315 can comprise any conducting material including, for example, gold, silver, platinum, indium-tin oxide, platinum black, conducting polymers, etc.

While electrodes 215, 315 are shown as being circular, it is understood that electrodes 215, 315 can have any shape. For example, when a flow module is included, electrodes 215, 315 can be elliptical or narrow lines that are oriented relative to the direction of flow (i.e., parallel, orthogonal, etc.). Cells can become oriented in a flowing system (usually elongated with the long axis in line with the flow). After wounding, differences in the cell healing might be detected on differently oriented electrodes allowing for the detection of cell alignment.

Cell cultures 218, 318 are shown located on electrode supports 212, 312 and in contact with electrodes 215, 315, respectively. This allows cell cultures 218, 318 to be wounded and/or monitored using electrical currents flowing through electrodes 215, 315. As shown in FIG. 6, for example, some or all of electrodes 315 can be used to wound cell culture 318. Similarly, some or all of electrodes 315 can be used to monitor cell culture 318. Alternatively, all electrodes 315 can be used to wound and monitor cell culture 318. While cell cultures 218, 318 are shown partially covering electrode supports 212, 312, it is understood that cells can completely or partially cover experiment wells 111, including that portion having counter electrode 113, as shown in FIG. 4.

Unlike other methods of wounding/monitoring that involve mechanical disruption of the cell layer, this invention allows a user to both wound and monitor the healing (cell migration) without any direct manipulation of the cell culture holder(s). Once placed in apparatus 20 shown in FIG. 1, cell culture holder(s) 26 can remain isolated until both the wounding and healing parts of the experiment are completed. This allows the cell culture to remain in an uninterrupted environment for the duration of an experiment. Additionally, because electrical wounding is more reproducible, experimental results are more verifiable and reliable.

Returning to FIG. 4, electricity can be applied to electrical connectors 110 by any known means, and can comprise either AC or DC current. The generation of electrical currents can be initiated by wounding module 30 and/or monitoring module 28. For example, a cell culture in contact with an electrode 115 can be wounded when wounding module 30 applies an elevated electrical field (i.e., high current) to the electrode 115. Additionally, monitoring module 28 can apply a low current to an electrode 115 and obtain readings of one or more electrical characteristics (e.g., voltage drop, impedance, resistance) to monitor a cell culture in contact with the electrode 115.

Figure 7:
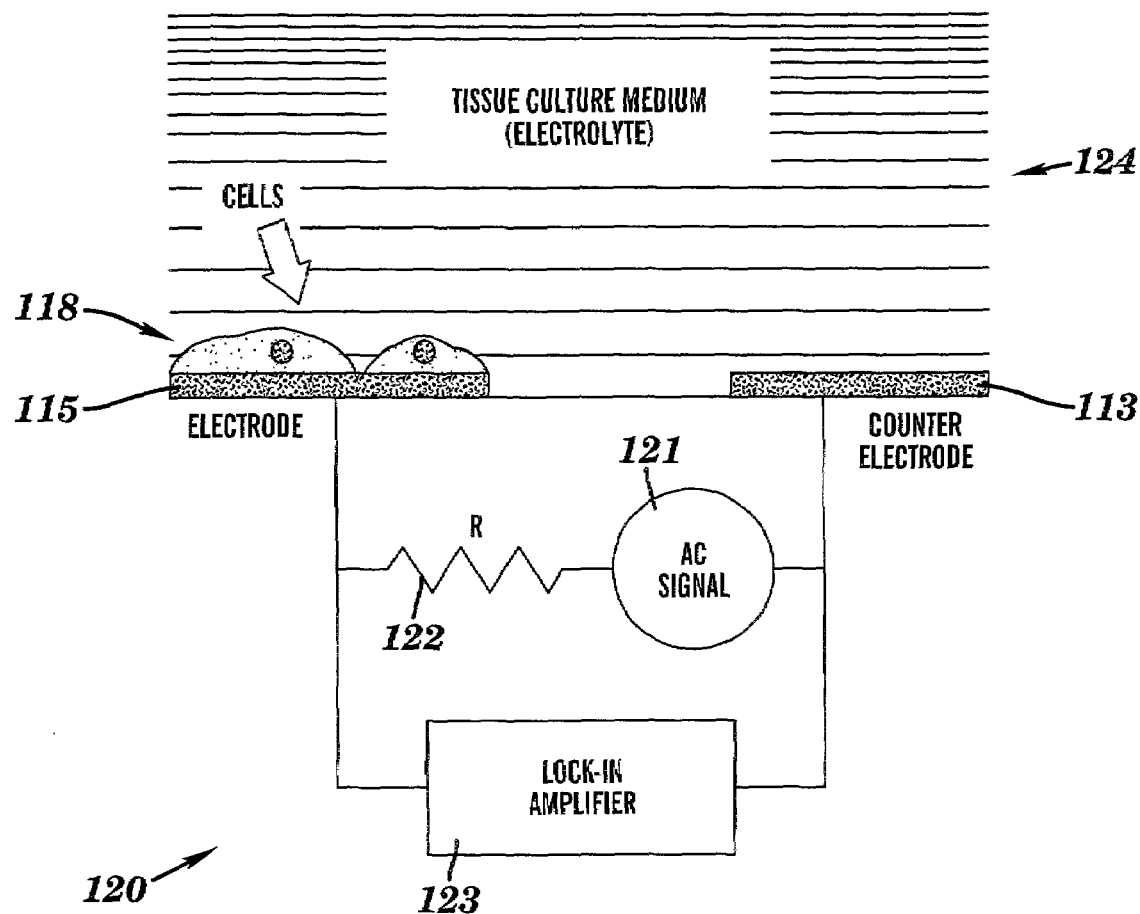
FIG. 7 is an AC circuit for performing both wounding and monitoring operations.

FIG. 7 shows an exemplary circuit 120 that can provide both wounding and monitoring of a cell culture 118 using an AC current applied to one or more electrodes 115. Current flows from electrode 115, through a tissue culture medium 124 and into counter electrode 113 to complete the circuit. Tissue culture medium 124 may comprise an electrically conductive medium, e.g., an electrolyte, to allow the circuit to complete.

To provide wounding, circuit 120 can briefly raise the current applied to electrode 115 to a level of, for example, a few milliamperes. For example, circuit 120 can apply a few volts from AC signal 121 through a 1,000 ohm series load resistance R 122. Since electrode 115 has an impedance of only a few thousand ohms at a high AC frequency (e.g., 40,000 Hz), the current will be in the range of a few milliamperes. In this example, the AC frequency can be within a range of frequencies between 10,000 and 60,000 Hz, although the invention is not limited to the use of these frequencies or AC current.

When wounding, some cells may not release from electrode 115. When this occurs, observation of the healing phase can be inhibited. To solve this problem, electroporation can be used. Electroporation allows for a shorter application time of the wounding current (for example 200 milliseconds instead of 10 seconds). When a high current is applied, a cell membrane is made permeable for a short period. By exposing the cell culture to a cytotoxic agent that is normally non permeant, the cells in contact with the electrode (and therefore made permeable) can be selectively killed.

For example, the cytotoxic agent bleomycin can be used. This compound has been used to evaluate the susceptibility of a membrane to become permeable due to electricity. Bleomycin or a similar agent is added to the culture medium at a concentration normally not affecting cell viability (e.g., a few nanomolar). The cells contacting electrode(s) 115 are then exposed to a brief (~200 msec) high current pulse, resulting in electroporation of the cells in contact with electrode(s) 115 and uptake of the compound. As a result, cells contacting electrode(s) 115 die and, over time, are replaced with the neighboring, non-electroporated, healthy cohorts.

When monitoring cell culture 118, circuit 120 can apply a reduced current to electrode 115. The current can be on a micro-ampere level, and can be altered by, for example, increasing the load resistance R 122 by a factor of about 1,000. It should be noted that any method for altering the current between wounding/monitoring can be utilized. For example, rather than altering the load resistance R 122, the current can be altered by increasing/decreasing the AC signal 121. Lock-in amplifier 123 can be placed in parallel with resistance R 122 and AC signal 121 to monitor one or more electrical characteristics of circuit 120. Lock-in amplifier 123 can comprise any system for monitoring, including, for example, a volt meter.

Figure 8:
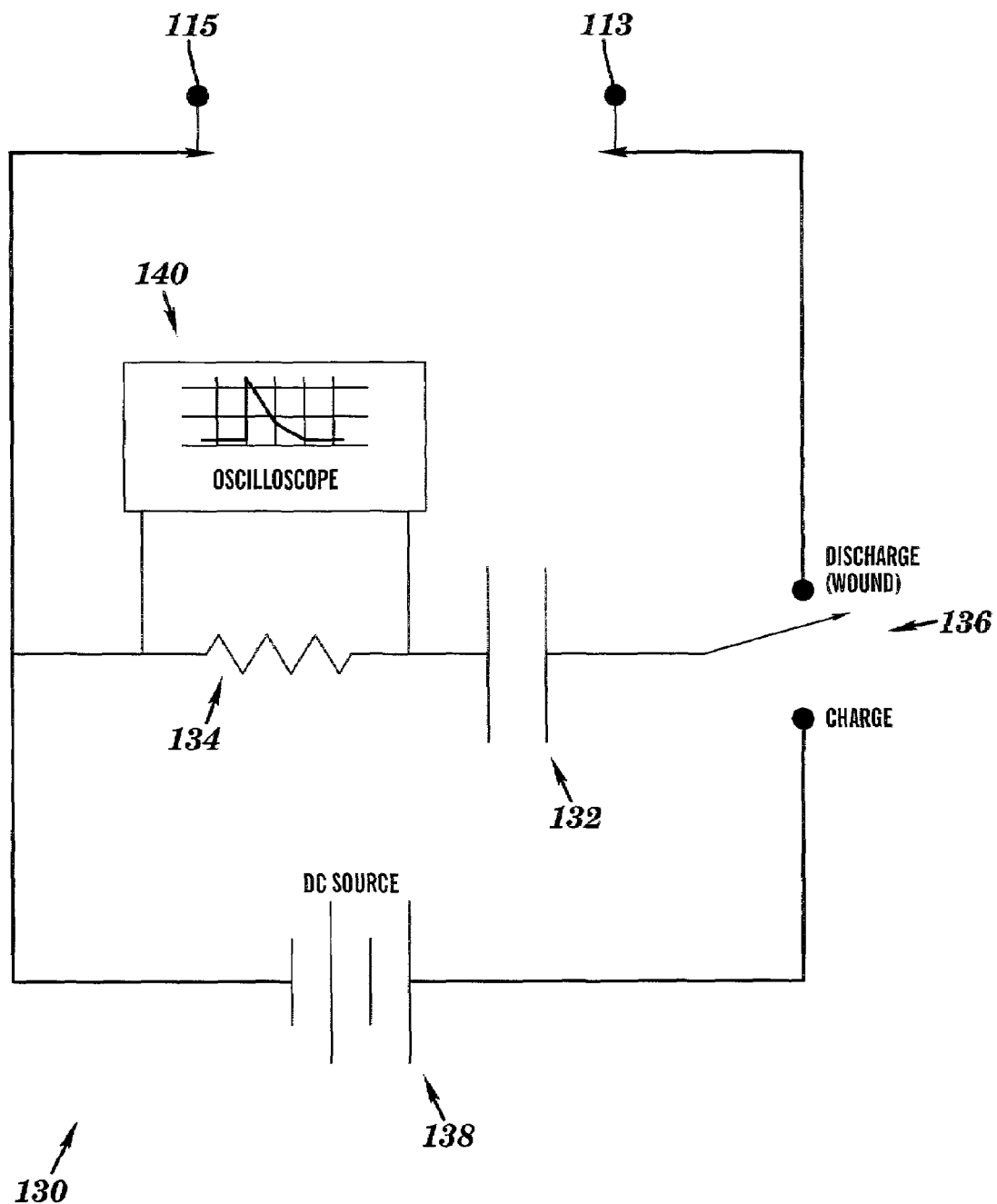
FIG. 8 is a DC circuit for performing a wounding operation.

Alternatively, FIG. 8 shows a DC circuit 130 that can be used for wounding a cell culture. DC circuit 130 includes an RC series circuit having a capacitor 132 and a resistor 134. A switch 136 can be used to select between charging and discharging capacitor 132. When charging capacitor 132, switch 136 is placed so that a circuit is formed that includes DC source 138 which provides DC current that charges capacitor 132. Once charged, switch 136 can be placed in an off position to break the circuit with DC source 138 and halt current flow.

When desired, switch 136 can be placed in the discharge (wound) position. In this case, the RC series circuit forms a circuit that flows through electrode 115, the cell culture, and counter electrode 113. In this configuration, the DC current flows through electrodes 113, 115 and falls off exponentially as determined by the RC time constant of the circuit and the impedance of the electrode(s). With this circuit, a user can choose a desired polarity, which can effect the wounding/healing process. Oscilloscope 140 can be placed in parallel with resistor 134 to monitor circuit 130 voltage and hence the current in circuit 130 as a function of time.

While the invention can use the same instrumentation (electrode) to both wound the cells and then to monitor the subsequent cell behavior (cell migrations/healing), it should be recognized that separate instrumentation (e.g., electrodes) for wounding and monitoring the cells can also be used. Moreover, the invention can comprise a system that only provides wounding of cell cultures.

In the invention, "wounding" refers to killing some of the cells in a cell culture. Cell death can be verified using an electrical current, a vital stain using a dye (i.e., calcein-AM), and/or other equivalent methods. As discussed above, electrical wounding can be done, for example, with an elevated AC current with or without a cytotoxic agent, or a DC pulse. When an elevated AC current is passed through an electrode, a high voltage drop (on the order of a few volts) results across the cells in contact with the electrode. This causes the cell membranes to break down (as in a brief current pulse used for electroporation). The high current also may result in localized heating. One of these events, or a combination of both, kills the cells. When a DC pulse is applied to an electrode, in addition to the above mechanisms, cells in contact with the electrode may also be killed as a result of the electrochemistry, for example, the build up of chlorine or of hydroxyl ions in the vicinity of the electrode.

Use of high frequency AC can result in the electrical field being applied more uniformly across a cell than when lower frequencies (e.g., 4,000 Hz) are used. For example, this is the case when, depending on the cell morphology, field strength is high near the central region of the attached cell but falls off closer to the outer edge of the cell (published PNAS Model). High frequency AC also can minimize the Faradaic voltage drop across the electrode-electrolyte interface resulting in a larger portion of the applied voltage appearing across the cells in contact with the electrode and not in a region below the cell layer.

"Healing" refers to the replacement of the killed cells with healthy cells from the neighboring region of the cell culture. Healthy cells migrate into the area previously occupied by the dead cells resulting in a change in one or more electrical characteristics. Healing can be monitored visually, photographically, with an electrical current, etc. The electrical current can be used to measure voltage, phase, or any other electrical characteristic. From this measurement, impedance, normalized resistance, etc. can be obtained, which in turn can be used to evaluate cell behavior such as cell migration time. For example, the circuit in FIG. 7 can measure electrical characteristic(s) between electrode 115 and counter electrode 113, which will vary based on the cell culture 118.

Figure 9:
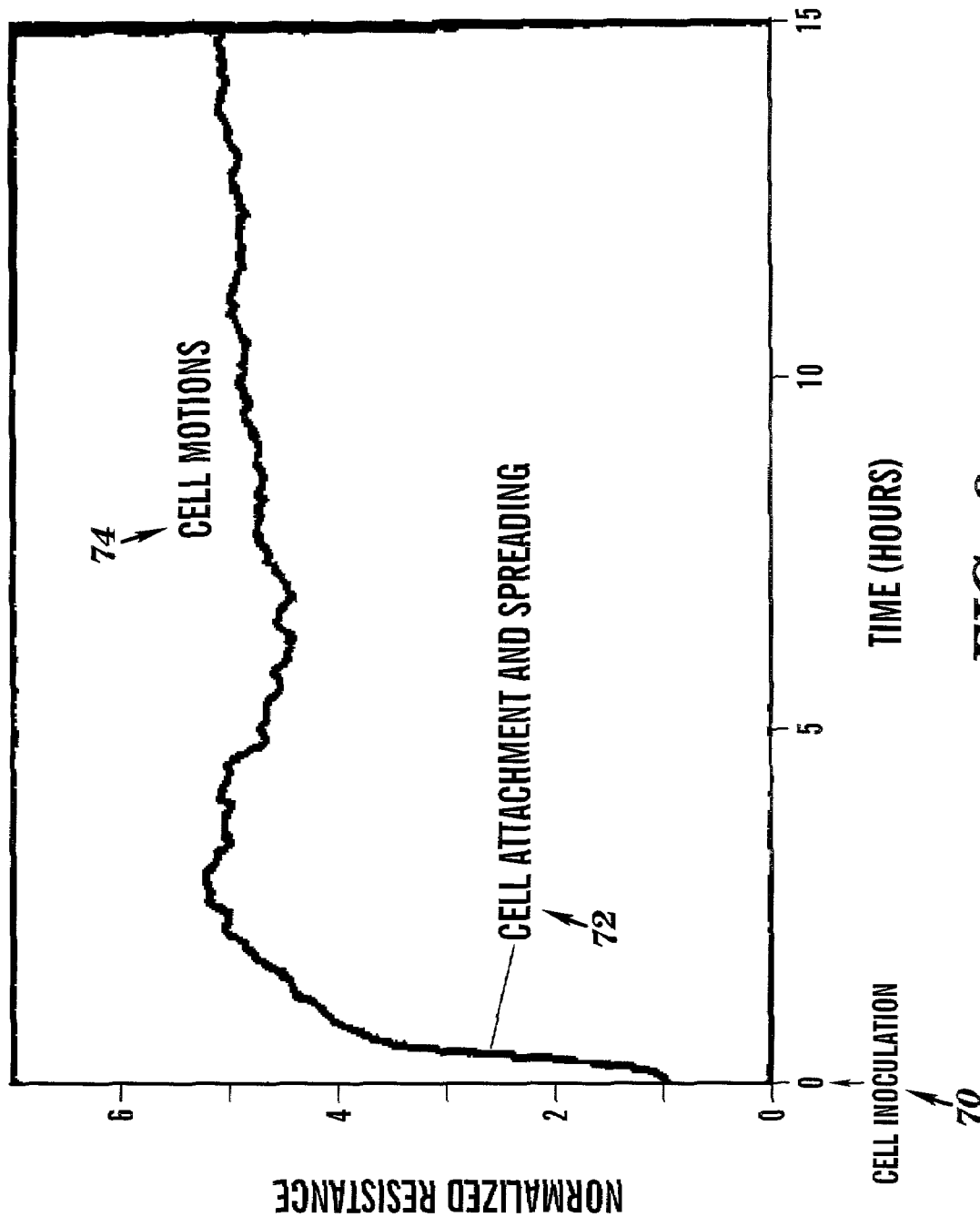
FIGS. 9-13 depict experimental data results.

FIG. 9 depicts a typical result of electrically monitored cell growth after cell inoculation. As shown, normalized resistance is plotted versus time with the cell inoculation 70 occurring at 0 hours. After cell inoculation 70, the surrounding cells went through a period of attachment and spreading 72. During this period, the normalized resistance increased substantially. However, after this period, the normalized resistance yielded relatively minor fluctuations due to the various cell motions 74.

Figure 10:
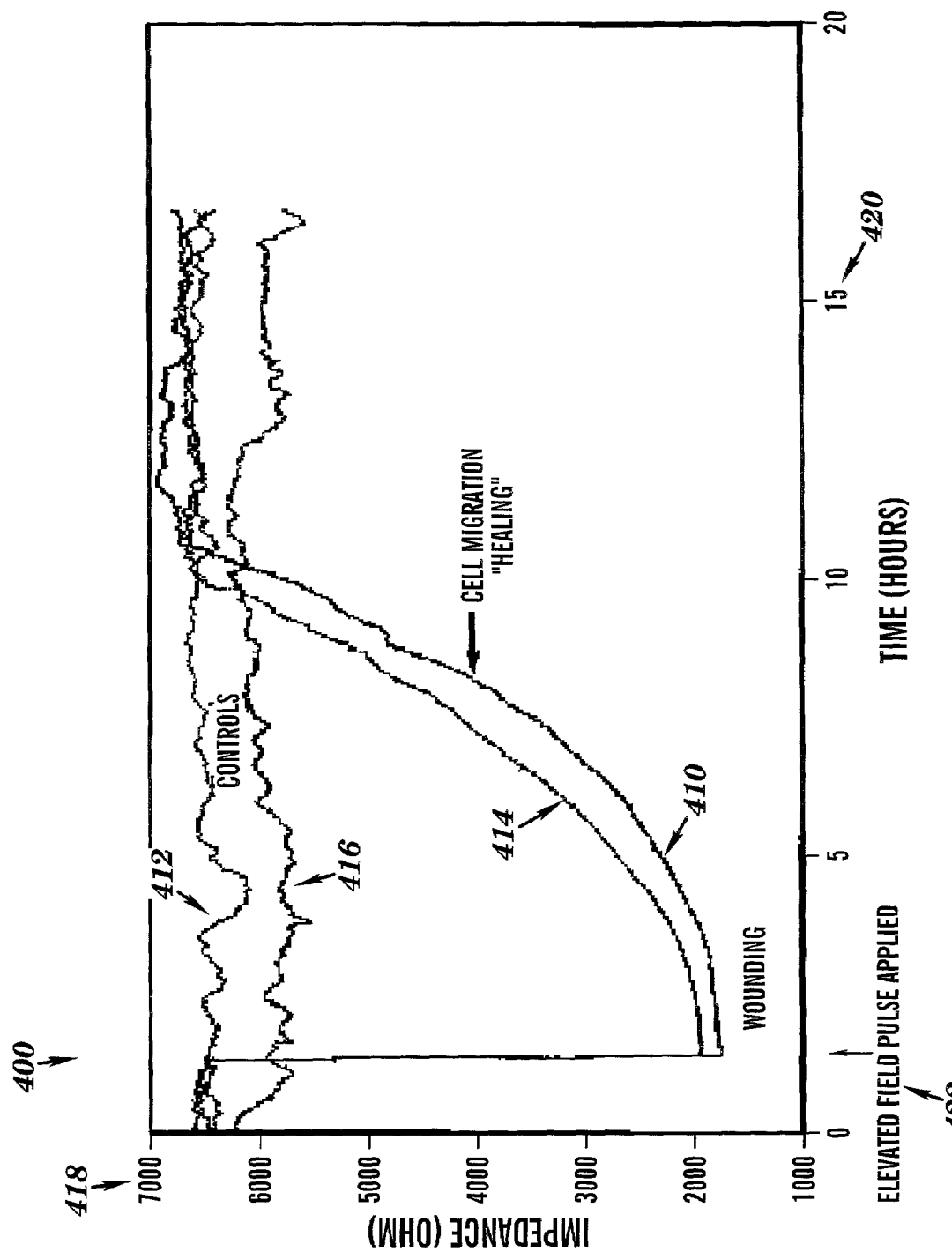

FIG. 10 shows a sample chart 400 created by a system implementing various aspects of the invention. Chart 400 plots an impedance 418 for each plot versus a time 420. Four plots, 410, 412, 414, 416 are shown. Each of the plots, 410, 412, 414, and 416 corresponds to a different cell culture. The cell cultures in this case were confluent layers of BSC-1 cells. As shown by an arrow 422, plots 410 and 414 received an elevated field pulse early in the experiment. As a result, the impedance for plots 410 and 414 dropped substantially. During the same period, the impedance for control plots 412 and 416 remained at roughly the same level. As time continued, the impedance for plots 410 and 414 recovered to roughly the same range as prior to the wounding. This data allows experimenters to infer numerous cell behaviors.

Figure 11:
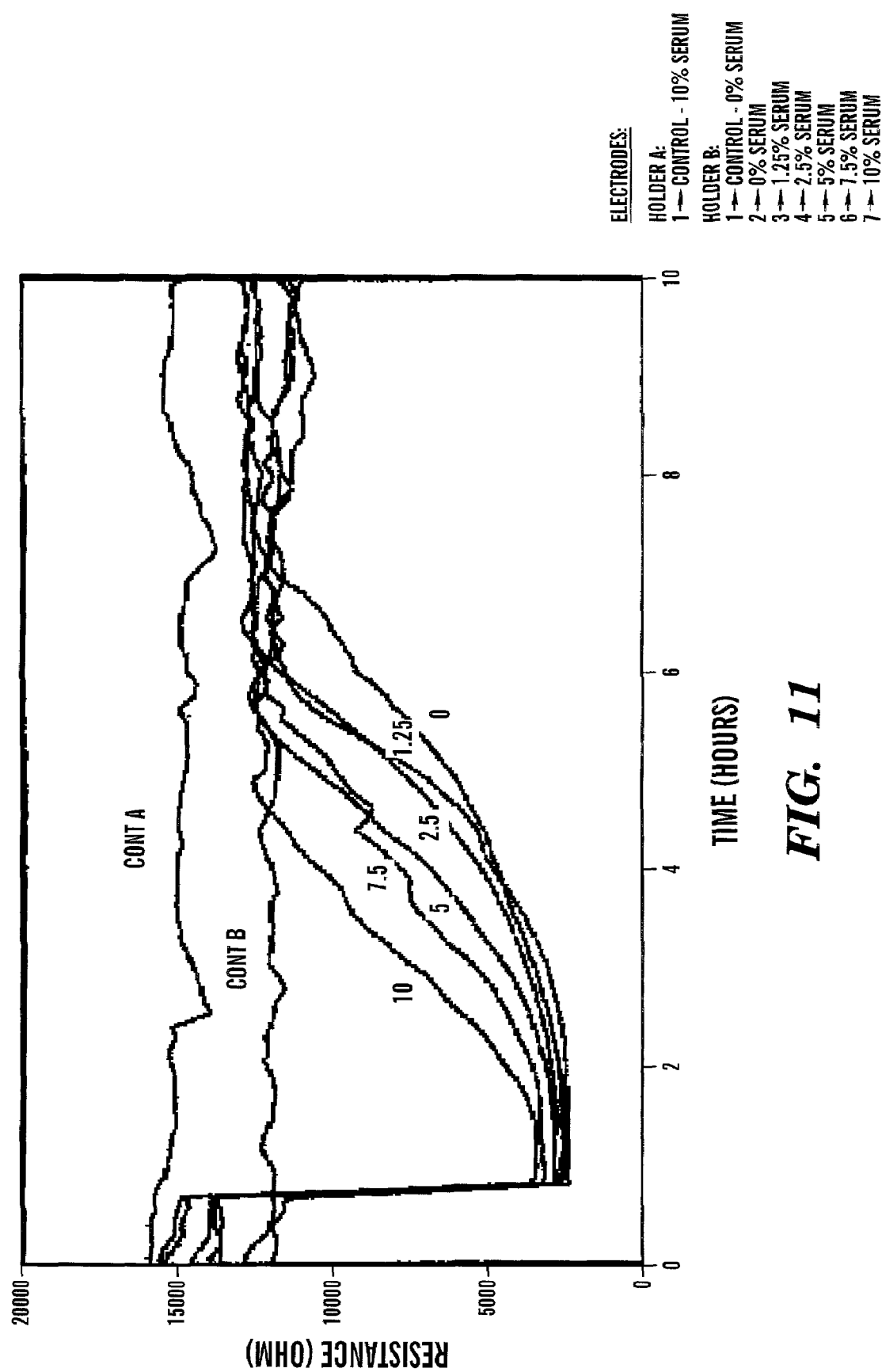

FIG. 11 shows results of another experiment in which wounding of confluent cell layers was performed using high AC current (milliamp range) in the presence of different levels of serum in the medium. In this case, confluent layers of cells were equilibrated overnight with medium containing different concentrations (in v/v percent) of fetal bovine serum. A wounding pulse is applied to holder B wells 1 through 7 about 0.8 hours into the data run shown. The six wounded cultures show rapid drop of resistance to that of cell free electrodes. Over the next few hours these curves return to control levels. The time required for this "healing" is clearly affected by the serum level.

Figure 12:
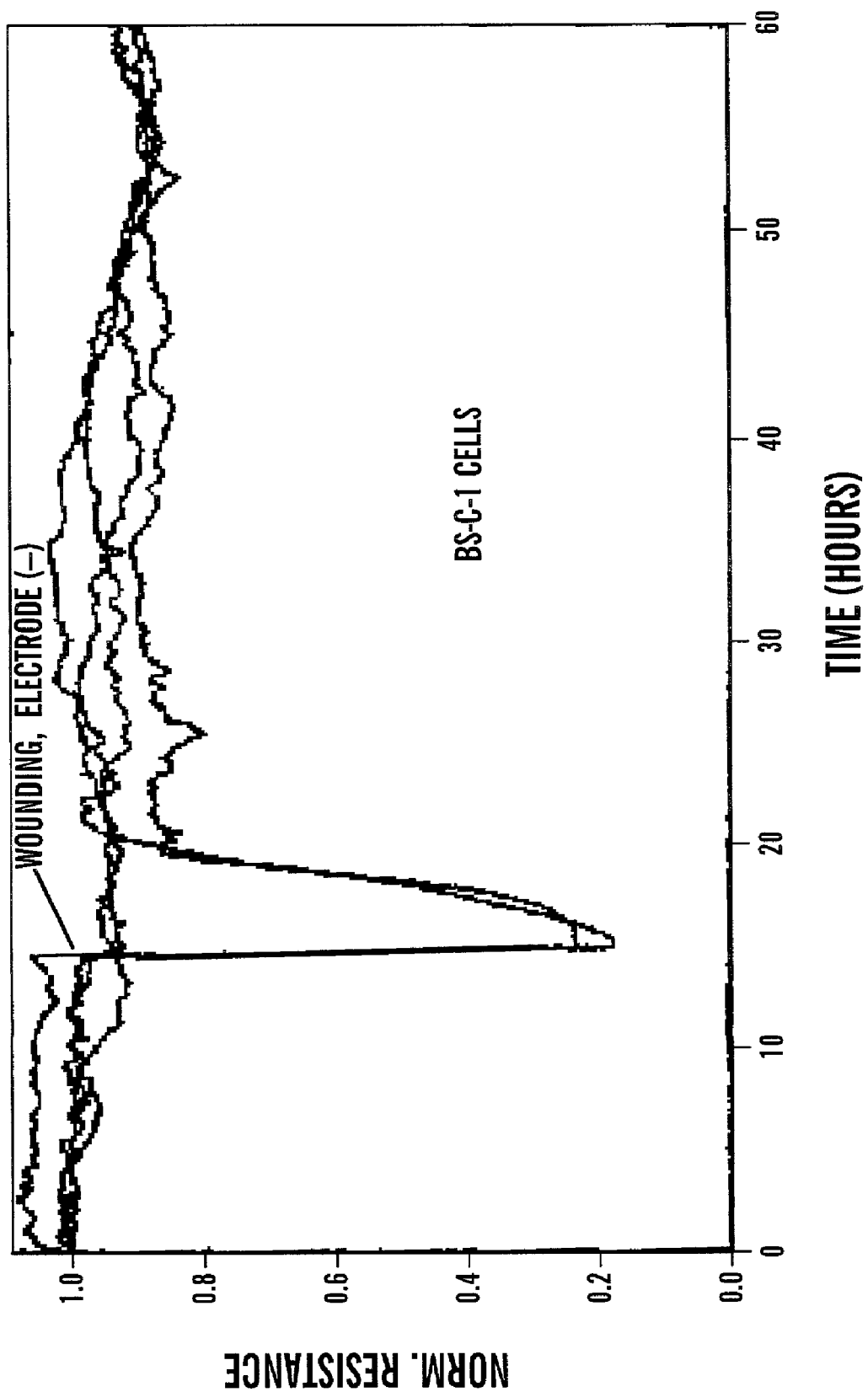
Figure 13:
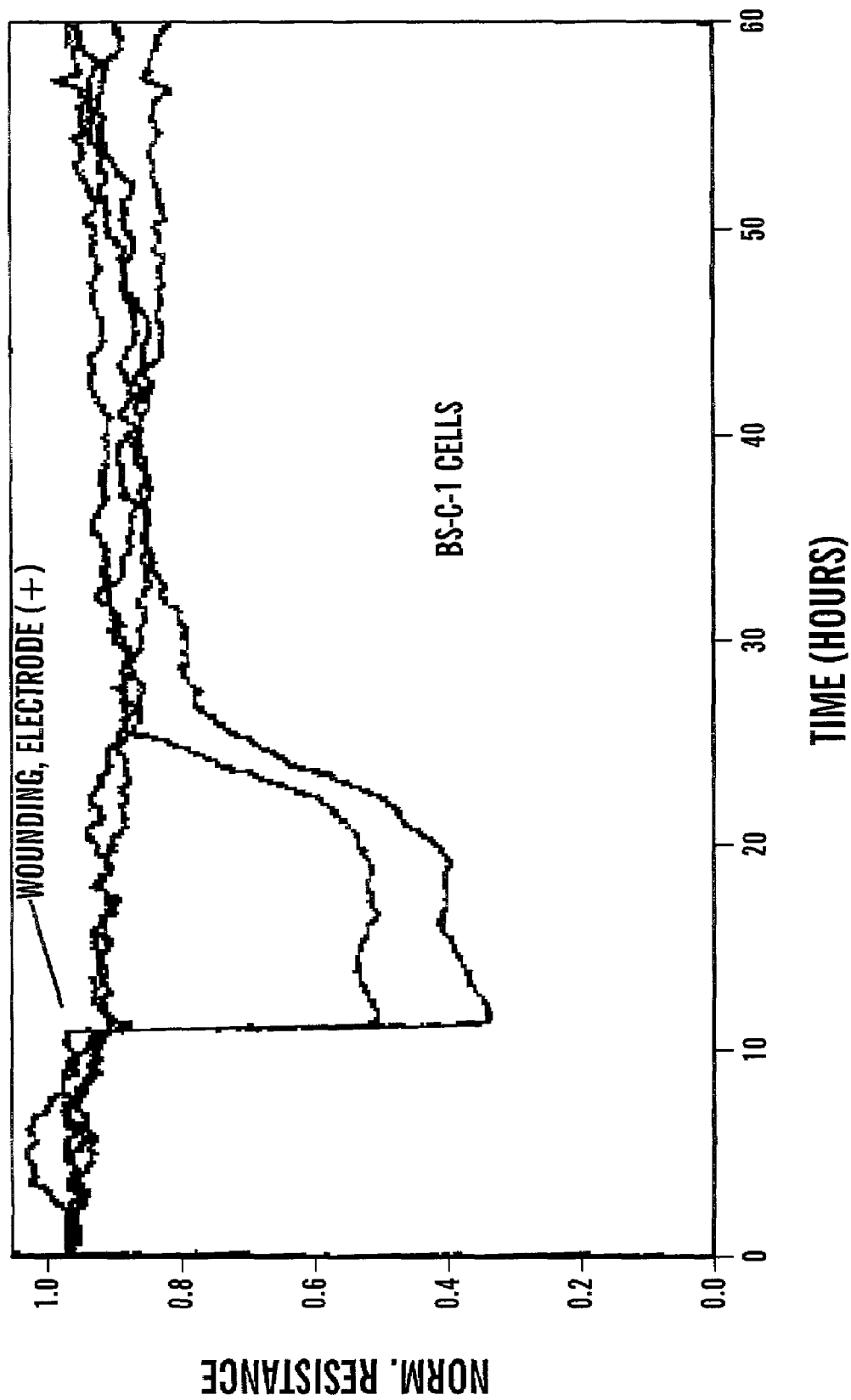

As discussed above, when DC current is used to wound a cell culture, the resulting cell behavior can vary based on the polarity used during wounding. FIGS. 12 and 13 depict experimental results when wounding is accomplished using DC currents of different polarity. When the wounding or small electrode(s) is/are positive (FIG. 13) during the current pulse, the recovery from the cell damage has been shown to require considerably more time than when the polarity is reversed, i.e., the wounding or small electrode(s) is/are negative (FIG. 12). This may be the result of electrochemical species that are produced at the electrode interface. Compared with AC wounding, the electrochemistry may play a larger role in both the cell killing and recovery (healing) in addition to electroporation effects and localized heating.

While the discussion herein uses electrical currents for wounding cell cultures, it is understood that other wounding methods can also be used. As previously discussed, cell cultures can be wounded by scratching a line or physically disrupting the cell culture. Other methods can be used to wound cell cultures in a more reproducible manner, for example, a laser can be used to wound the cell culture while it is electrically monitored.

It is understood that the components of the present invention can be realized in hardware, software, or a combination of hardware and software. Any kind of computer—or other apparatus adapted for carrying out the methods described herein—is suited. A typical combination of hardware and software could be a general purpose computer with a computer program that, when loaded and executed, carries out the methods described herein. Alternatively, a specific use computer, containing specialized hardware for carrying out one or more of the functional tasks of the invention could be utilized. Aspects of the present invention can also be embedded in a computer program product, which comprises all the features enabling the implementation of the methods described herein, and which—when loaded in a computer—is able to carry out these methods. Computer program, software program, program, module, mechanism or software, in the present context mean any expression, in any language, code or notation, of a set of instructions intended to cause a system having an information processing capability to perform a particular function either directly or after either or both of the following: (a) conversion to another language, code or notation; and/or (b) reproduction in a different material form.

The foregoing description of various aspects of the invention has been presented for purposes of illustration and description. It is not intended to be exhaustive or to limit the invention to the precise form disclosed, and obviously, many modifications and variations are possible. Such modifications and variations that may be apparent to a person skilled in the art are intended to be included within the scope of the invention as defined by the accompanying claims.

What is claimed is:

1. A method of processing a cell culture, comprising:
maintaining an uninterrupted environment in a holding device during a wounding and monitoring process, wherein the holding device includes at least one well for holding the cell culture, and wherein the at least one well includes at least one exposed electrode that contacts the cell culture;
wounding the cell culture, wherein the wounding includes applying an alternating current (AC) electrical field having a frequency of at least ten thousand Hertz and a current of approximately three milliamperes to the at least one electrode; and
monitoring the cell culture while the cell culture is in the holding device.

2. The method of claim 1, wherein the monitoring uses the at least one electrode.

3. The method of claim 1, wherein the monitoring includes measuring at least one electrical characteristic between the at least one electrode and a counter electrode.

4. The method of claim 1, wherein the wounding further includes exposing the cell culture to a cytotoxic agent.

5. The method of claim 1, wherein the frequency is in a range of approximately ten thousand Hertz to approximately sixty thousand Hertz.

6. A method of wounding a cell culture, comprising:
holding the cell culture in at least one well of a holding device, the at least one well having at least one exposed electrode that contacts the cell culture; and
wounding the cell culture using the at least one electrode, wherein the wounding includes applying an alternating current (AC) electrical field having a frequency of approximately forty thousand Hertz to the at least one electrode.

7. The method of claim 6, wherein the AC electrical field further comprises a current of approximately three milliamperes.

8. The method of claim 6, wherein the wounding further includes exposing the cell culture to a cytotoxic agent.

9. The method of claim 6, wherein the applying comprises a duration of approximately two hundred milliseconds.

10. A method of processing a cell culture, comprising:
wounding the cell culture using at least one electrode, wherein the wounding includes applying a first alternating current (AC) electrical field having a frequency of at least ten thousand Hertz to the at least one electrode; and
monitoring the cell culture using the at least one electrode by applying a second AC electrical field to the at least one electrode.

11. The method of claim 10, wherein the wounding further includes exposing the cell culture to a cytotoxic agent.

12. The method of claim 10, wherein the first AC electrical field further has a current of approximately three milliamperes.

13. The method of claim 10, wherein the second AC electrical field comprises a current of approximately three micro-amperes.

14. The method of claim 10, farther comprising maintaining an uninterrupted environment in a holding device during the wounding and the monitoring.

15. The method of claim 10, wherein a computer automatically controls the wounding and the monitoring.

* * * * *